United States Patent
Kershman et al.

(10) Patent No.: US 12,053,535 B1
(45) Date of Patent: Aug. 6, 2024

(54) LIP BALM CONTAINING CAFFEINE, NICOTINE OR TESTOSTERONE

(71) Applicants: Alvin Kershman, Chesterfield, MO (US); Jeff Shear, Bonita Springs, FL (US); Doreen Linze, Labadie, MO (US)

(72) Inventors: Alvin Kershman, Chesterfield, MO (US); Jeff Shear, Bonita Springs, FL (US); Doreen Linze, Labadie, MO (US)

(73) Assignee: Shear Kershman Laboratories, Inc., Chesterfield, MO (US)

( * ) Notice: Subject to any disclaimer, the term of this patent is extended or adjusted under 35 U.S.C. 154(b) by 56 days.

(21) Appl. No.: 17/403,679

(22) Filed: Aug. 16, 2021

Related U.S. Application Data

(63) Continuation-in-part of application No. 16/538,866, filed on Aug. 13, 2019, now abandoned.

(60) Provisional application No. 62/718,261, filed on Aug. 13, 2018.

(51) Int. Cl.
  *A61K 8/02* (2006.01)
  *A61K 8/49* (2006.01)
  *A61K 8/63* (2006.01)

(52) U.S. Cl.
  CPC .......... *A61K 8/0216* (2013.01); *A61K 8/4926* (2013.01); *A61K 8/4953* (2013.01); *A61K 8/63* (2013.01); *A61K 2800/412* (2013.01); *A61K 2800/52* (2013.01); *A61K 2800/596* (2013.01); *A61K 2800/92* (2013.01)

(58) Field of Classification Search
  CPC .. A61K 8/0216; A61K 8/4926; A61K 8/4953; A61K 8/63; A61K 2800/412; A61K 2800/52; A61K 2800/596; A61K 2800/92
  See application file for complete search history.

(56) References Cited

U.S. PATENT DOCUMENTS

| 4,606,913 | A | * | 8/1986 | Aronson | A61Q 19/00 516/29 |
| 4,751,075 | A | * | 6/1988 | Chernowsky | A61K 9/0014 514/474 |
| 5,382,436 | A | * | 1/1995 | Potts | A61K 31/52 424/769 |
| 7,560,465 | B2 | * | 7/2009 | Holschen | A61Q 19/00 514/263.34 |

FOREIGN PATENT DOCUMENTS

EP  0474270 A1 * 3/1992 ............. A61K 8/553

OTHER PUBLICATIONS

Atmos 300K Datasheet [online]. Ruger Chemical Company, Inc. [retrieved on 2020-09-21]. Retrieved from the Internet: < URL: https://www.ulprospector.com/en/na/Food/Detail/881/978389/Atmos-300K>. (Year: 2005).*

* cited by examiner

*Primary Examiner* — Mina Haghighatian
*Assistant Examiner* — Janice Y Silverman
(74) *Attorney, Agent, or Firm* — Linda L. Lewis

(57) ABSTRACT

A lip balm providing a caffeine, nicotine or testosterone active, where the lip balm contains at least one lipid in the range of about 30 wt. % to 60 wt. %; a surfactant in the range of about 60 wt. % to 25 wt. %; caffeine, nicotine or testosterone active in the range of about 1 to 40 wt. %; and less than 1.0 wt. % water, where the lip balm, when applied to a lip, delivers the active in less than about ten minutes.

12 Claims, No Drawings

LIP BALM CONTAINING CAFFEINE, NICOTINE OR TESTOSTERONE

CROSS-REFERENCE TO RELATED APPLICATIONS

This application claims the benefit of provisional patent application 62/718,261 filed Aug. 13, 2018, which is hereby incorporated by reference, and is a Continuation-in-Part of utility patent application Ser. No. 16/538,866 filed Aug. 13, 2019, which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to a lip balm formulation, and more particularly to a lip balm formulation having a high emulsifier-content caffeine or testosterone delivery system.

Related Art

The present invention provides a caffeinated formulation capable of being topically administered to a mucous membrane surface of the body as a caffeinated lip balm that may be applied to the mucous membrane surface of lip skin. It also provides a testosterone formulation.

U.S. Pat. No. 7,560,465 discloses a lip balm that delivers dissolved caffeine. The caffeine is dissolved in a solvent (water) which is then dispersed in a lipid or wax to make the lip balm. Prior art lip balms used micronized particles of caffeine. This patent fails to even mention a surfactant as part of the lip balm composition.

U.S. Pat. No. 5,085,856 discloses a cosmetic water-in-oil emulsion lipstick comprising a phospholipid and glycerol fatty acid esters emulsifying system. This patent teaches away from using greater than about 10% emulsifier in its lipstick.

U.S. Pat. No. 6,663,853 discloses a lip care moisturizing product in the form of a water-in-oil emulsion, containing at least one fatty acid ester, at least one wax, the total of said at least one fatty acid ester and said at least one wax being at least about 1.0%, liposomes containing water therein, and an emulsifier. The emulsifier content is up to 7.5%.

WO9426234 Patent Application discloses water-in-oil emulsions having a petrolatum base for use as lip balm compositions. The emulsions contain up to about 5 weight percent water and are preferably formulated as microemulsions. The compositions preferably also contain a wax, an oil, and a humectant component. The emulsions contain up to 10% surfactants. The present invention is neither taught nor suggested in the above cited references.

SUMMARY OF THE INVENTION

The lip balm formulation of the present invention comprises at least one lipid, at least one surfactant, and one of caffeine, nicotine or testosterone, or a combination thereof. The formulation contains greater than about 10 wt. % surfactant. In a preferred embodiment, the formulation contains greater than about 25 wt. % surfactant. In a more preferred embodiment, the formulation contains from about 25 to 60 wt. % surfactant. In another preferred embodiment, the formulation contains from about 30 to 60 wt. % surfactant.

In a preferred embodiment, the components are present in the formulation such that the w/w ratio of surfactant to lipid is in the range of from about 3/1 to 1/3. In a more preferred embodiment, the lipid is present in the range of about 30 wt. % to 60 wt. %; the surfactant is present in the range of about 60 wt. % to 25 wt. %, and the caffeine, nicotine or testosterone is present in the range of about 0.1 to 40 wt. %. Preferably, caffeine is present in the formulation from about 5 to 40 wt. %. Nicotine or testosterone are present in the formulation of from about 0.1 to 30 wt. %. In a more preferred embodiment, the formulation includes other excipients including stabilizers, melting point adjusters, oils, flavorings, colorings, sun screens, additional nutrients or pharmaceuticals, and glycerine.

The lip balm does not contain an aqueous phase. The water content of the lip balm is less than 1.0 wt. %. Preferably, the water content is less than 0.8 wt. %, and more preferably, the water content is less than about 0.5 wt. %.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE PREFERRED EMBODIMENTS

The following description of the preferred embodiment(s) is merely exemplary in nature and is in no way intended to limit the invention, its application, or uses. The present invention provides a caffeinated formulation capable of being topically administered to a mucous membrane surface of the body as a caffeinated lip balm that may be applied to the surface of lip skin. Thus, one can combine the standard benefits of a lip balm, such as protecting the lips from heat, cold, sun and wind, with providing a dose of caffeine sufficient to improve alertness. This invention also provides a testosterone and a nicotine formulation.

The lipids of the present invention may be of animal, vegetable or mineral origin, which are water-insoluble, inert, non-toxic hydrocarbon fats and oils and derivatives thereof, and may comprise any of the commonly commercially available fats or oils approved by the Food & Drug Administration, having melting points in the range of about 90 to 160° F. The lipid may comprise a vegetable oil base commonly known as hard butter. Hard butters are hydrogenated, press fractionated or other processed oils that are processed or recombined to have a solid fat index (percent solid fat vs. temperature) similar to that of cocoa butter. However, other lipids may be used that are relatively hard or solid at room temperature, but melt rapidly in the mouth at a temperature of about 98° F. (mouth temperature). In a preferred embodiment, the lipid is employed in the amounts within the range of from about 30 to 60 wt. %.

Examples of suitable lipids include tallow, hydrogenated tallow, hydrogenated vegetable oil, almond oil, coconut oil, corn oil, cottonseed oil, light liquid petrolatum, heavy liquid petrolatum, olein, olive oil, palm oil, peanut oil, persic oil, sesame oil, vitamin E, soybean oil or safflower oil. Additionally, stearines can be used as a lipid in the present invention. The addition of stearines to the product provides the favorable property of mold-release. Further, the addition of stearines raise the melting point of the composition as high as about 100.degree. F., which is particularly beneficial when the product is shipped or stored in unrefridgerated compartments.

Preferred examples include petrolatum, a mineral oil (Vaseline oil), which may be any petroleum based product; modified or unmodified vegetable oils such as peanut oil, wheat germ oil, linseed oil, jojoba oil, apricot kernel oil, walnut oil, palm oil, pistachio oil, sesame oil, colza oil, cade oil, corn germ oil, peach kernel oil, poppy seed oil, pine oil, castor oil, soya oil, safflower oil, coconut oil, hazelnut oil, grapeseed oil, avocado oil, soy oil, sweet almond oil, calophyllum oil, castor oil, olive oil, sunflower oil, or animal oils such as whale oil, seal oil, menhaden oil, halibut liver oil, cod liver oil, cod, tuna, turtle tallow, horse's hoof, sheep's foot, mink, otter, marmot oil and the like; synthetic oils such as silicon oil such as dimethylpolysiloxane; alkyl and alkenyl esters of fatty acids, such as isopropyl esters of myristic, palmitic and stearic acids and fatty esters which are solid at room temperature; waxes such as lanolin wax, candelilla wax, spermaceti, cocoa butter, karite butter, silicon waxes, hydrogenated oils which are solid at room temperature, sucro-glycerides, oleates, myristates, linoleates, stearates, paraffin, beeswax, carnauba wax, ozokerite, candelilla wax, microcrystalline wax; fatty alcohols such as lauryl, cetyl, myristyl, stearyl, palmityl and oleyl alcohols; polyoxyethylated fatty alcohols; and wax esters, lanolin and its derivatives, perhydrosqualene and saturated esters, ethyl palmitate, isopropyl palmitate, alkyl myristates such as isopropyl myristate, butyl myristate and decyl myristate, hexyl stearate, triglyceride esters, triglycerides of octanoic and decanoic acid, cetyl ricinoleate, stearyl octanoate (Purcellin oil), fatty acids, polyhydric alcohols, polyether derivatives, fatty acid monoglycerides, and hydrogenated palm oil (PARAMOUNT XX and PARAMOUNT X oil), and mixtures of waxes and oils. The preferred lipids are a combination of hydrogenated palm oil and vitamin E. The preferred oils contain less than about 0.2 wt. % water.

Any emulsifier or surfactant or combination thereof approved for use in foods by the Food and Drug Administration and having a relatively low HLB value, in the range of about 0 to 6, is suitable for use in the present invention. The appropriate surfactant minimizes the surface tension of the lipid, allowing it to oil wet and encapsulate the non-oil solid particles. Suitable surfactants include alkyl aryl sulfonate, or alkyl sulfonates, or sulfonated amides or amines, or sulfated or sulfonated esters or ethers, or alkyl sulfonates, of dioctyl sulfonosuccinate and the like, or a hydrated aluminum silicate such as bentonite or kaolin, triglycerol monostearate, triglycerol monoshortening, mono- and di-glyceride and propylene glycol with an HLB of less than 4, octaglycerol monooleate, octaglyceron monostearate, and decaglycerol decaloeate.

The surfactant is preferably a non-water soluble surfactant having an HLB number of less than about 6, and includes emulsifiers. A preferred surfactant is commercially sold as ATMOS® 300K, and is a combination of mono- and di-glycerides made from edible food sources and propylene glycol with an HLB of 2.8. Another preferred surfactant is Defospum E100, a defoamer which is a combination of mono- and di-glycerides sold by Defotec. A third preferred surfactant is Lucrafoam E100, a defoamer which is a combination of mono-, di- and tri-glycerides sold by Levaco Chemicals.

The lip balm may also include other pharmaceutically acceptable agents, such as sweetening agents, including hydrogenated starch hydrolysates, synthetic sweeteners such as sorbitol, xylitol, saccharin salts, L-aspartyl-L-phenylalanine methyl ester, as well as coloring agents, other binding agents, lubricants, such as calcium stearate, stearic acid, magnesium stearate, antioxidants such as butylated hydroxyl-toluene and the like. A sunscreen, well known in the art, can also be added to the lip balm. A stabilizer, such as 27 STEARINE, a glyceryl tristearate may also be used.

The caffeine, nicotine or testosterone can be added in any suitable form. A solution of caffeine or micronized caffeine particles may be used.

The lip balm is prepared by means well known in the art. A preferred method is melting the lipid and mixing in the remaining ingredients, then allowing the mixture to cool.

The lip balm formulation contains greater than 10 wt. % surfactant. In a preferred embodiment, the lipid and surfactant components are present in the formulation such that the w/w ratio of surfactant to lipid is in the range of from about 2/1 to 1/2. In a more preferred embodiment, the lipid is present in the range of about 30 wt. % to 60 wt. %; the surfactant is present in the range of about 60 wt. % to 25 wt. %, and the active is present in the range of about 1 to 40 wt. %.

The lip balm delivers the nicotine or caffeine to the body rapidly, typically in less than about one (1) minute, and preferably in less than about 45 seconds. Testosterone is typically delivered in less than about ten (10) minutes, and preferably from about one (1) to ten (10) minutes.

An Example of the Invention

A lip balm was prepared according to the following list of ingredients.

| Example 1-Testosterone | | |
| --- | --- | --- |
| Ingredient | Weight | % |
| ATMOS 300K (surfactant) | 80.00 | 40.00% |
| PARAMOUNT XX (lipid) | 59.00 | 29.50% |
| Testosterone USP 24 | 40.00 | 20.00% |
| 27 STEARINE (stabilizer) | 16.00 | 8.00% |
| NOVATOL 5-87 Vitamin E (surfactant) | 5.00 | 2.50% |

| Example 2-Caffeine | | |
| --- | --- | --- |
| Ingredient | Weight | % |
| Caffeine Anhydrous | 120.00 | 20.00% |
| ATMOS 300K | 240.00 | 40.00% |
| PARAMOUNT XX | 183.00 | 30.50% |
| 27 STEARINE | 48.00 | 8.00% |
| Cinnamon Oil, concentrated, O.S. | 9.00 | 1.50% |

| Control 3-Caffeine | | |
| --- | --- | --- |
| Ingredient | Weight | % |
| ATMOS 300K | 40.00 | 50.00% |
| PARAMOUNT XX | 7.00 | 8.75% |
| 27 STEARINE | 1.50 | 1.875% |
| Caffeine Anhydrous | 20.00 | 25.00% |

Control 3-Caffeine

| Ingredient | Weight | % |
|---|---|---|
| Smitty Bee Amber Honey, USDA Grade A | 10.00 | 12.50% |
| Cinnamon Flavor O.S. | 1.50 | 1.875% |

Example 4-Caffeine

| Ingredient | Weight | % |
|---|---|---|
| PARAMOUNT XX | 64.80 | 32.40% |
| ATMOS 300K | 56.00 | 28.00% |
| 27 STEARINE | 17.20 | 8.60% |
| Bickford Cinnamon Flavor | 3.40 | 1.70% |
| Powdered Sugar | 30.00 | 15.00% |
| Sucralose pharma, powder | 0.60 | 0.30% |
| Caffeine | 28.00 | 14.00% |

Example 5-Caffeine

| Ingredient | Weight | % |
|---|---|---|
| PARAMOUNT X | 80.00 | 40.00% |
| ATMOS 300K | 82.00 | 41.00% |
| 27 STEARINE | 14.00 | 7.00% |
| Sucralose pharma, powder | 2.00 | 1.00% |
| Cinnamon Oil, concentrated, O.S. | 2.00 | 1.00% |
| Caffeine Anhydrous | 20.00 | 10.00% |

Example 6 Nicotine

| Ingredient | Weight | % |
|---|---|---|
| ATMOS 300K | 60.00 | 30.00% |
| PARAMOUNT XX | 89.00 | 44.50% |
| 27 STEARINE | 20.00 | 10.00% |
| Nicotine (Under Argon) | 20.00 | 10.00% |
| Peppermint Terpeneless Oil | 1.00 | 0.50% |
| Vitamin E 1300IU (Natural Source) | 10.00 | 5.00% |

Example 7 Nicotine

| Ingredient | Weight | % |
|---|---|---|
| Nicotine (Under Argon) | 2.0 | 2.00% |
| PARAMOUNT XX | 35.0 | 35.00% |
| 10X Refined Powdered Sugar | 20.2 | 20.20% |
| ATMOS 300K | 40.0 | 40.00% |
| SNC-1 Flavor Concentrate | 0.3 | 0.30% |
| 27 STEARINE | 2.5 | 2.50% |

Example 8 Nicotine

| Ingredient | Weight | % |
|---|---|---|
| Nicotine (Under Argon) | 3.0 | 1.00% |
| PARAMOUNT XX | 112.2 | 37.40% |
| 10X Refined Powdered Sugar | 75.0 | 25.00% |
| ATMOS 300K | 105.0 | 35.00% |
| SNC-1 Flavor Concentrate | 0.9 | 0.30% |
| 27 STEARINE | 3.0 | 1.00% |
| Sucralose pharma, powder | 0.9 | 0.30% |

Example 9-Nicotine

| Ingredient | Weight | % |
|---|---|---|
| Nicotine (Under Argon) | 1.0 | 0.50% |
| PARAMOUNT XX | 78.0 | 39.00% |
| 10X Refined Powdered Sugar | 48.0 | 24.00% |
| ATMOS 300K | 68.4 | 34.20% |
| SNC-1 Flavor Concentrate | 1.2 | 0.60% |
| 27 STEARINE | 3.0 | 1.50% |
| Sucralose pharma, powder | 0.4 | 0.20% |

Example 10-Nicotine

| Ingredient | Weight | % |
|---|---|---|
| Nicotine (Under Argon) | 2.0 | 1.00% |
| PARAMOUNT XX | 77.2 | 38.60% |
| 10X Refined Powdered Sugar | 50.0 | 25.00% |
| ATMOS 300K | 66.0 | 33.00% |
| SNC-1 Flavor Concentrate | 1.2 | 0.60% |
| 27 STEARINE | 3.0 | 1.50% |
| Sucralose pharma, powder | 0.6 | 0.30% |

Example 11-Nicotine

| Ingredient | Weight | % |
|---|---|---|
| Nicotine (Under Argon) | 1.0 | 0.50% |
| PARAMOUNT XX | 82.0 | 41.00% |
| 10X Refined Powdered Sugar | 43.0 | 21.50% |
| ATMOS 300K | 72.4 | 36.20% |
| SNC-1 Flavor Concentrate | 1.2 | 0.60% |
| Sucralose pharma, powder | 0.4 | 0.20% |

Example 12 - Nicotine

| Ingredient | Weight | % |
|---|---|---|
| Nicotine (Under Argon) | 1.0 | 0.50% |
| PARAMOUNT XX | 93.6 | 46.80% |
| 10X Refined Powdered Sugar | 20.0 | 10.00% |
| ATMOS 300K | 80.0 | 40.00% |
| SNC-1 Flavor Concentrate | 1.2 | 0.60% |
| 27 STEARINE | 3.0 | 1.50% |
| Sucralose pharma, powder | 0.4 | 0.60% |

Example 13 - Nicotine

| Ingredient | Weight | % |
|---|---|---|
| PARAMOUNT XX | 54.30 | 27.15% |
| PARAMOUNT X | 18.10 | 9.05% |
| ATMOS 300K | 67.00 | 33.50% |
| Orange Cream Flavor Oil | 4.00 | 2.00% |
| 27 STEARINE | 4.00 | 2.00% |

-continued

Example 13 - Nicotine

| Ingredient | Weight | % |
| --- | --- | --- |
| Powdered Sugar | 36.00 | 18.00% |
| Sucralose pharma, powder | 0.60 | 0.30% |
| Nicotine (Under Argon) | 16.00 | 8.00% |

Testing of Example 7

The lip balm of Example 7 was tested for effectiveness in administering nicotine. Push tubes of the lip balm were provided to ten (10) test subjects who were trained to detect and note the time to sense the nicotine in their system (the time to satisfaction). Each dose provided about 60 mg of lip balm delivering 1.2 mg of Nicotine to the lips. The time to satisfaction for each test subject is given below.

| Sample # | Time to Satisfaction Seconds |
| --- | --- |
| 1 | 20 |
| 2 | 25 |
| 3 | 40 |
| 4 | 55 |
| 5 | 20 |
| 6 | 32 |
| 7 | 28 |
| 8 | 30 |
| 9 | 26 |
| 10 | 35 |
| | Mean: 31.1 Seconds |
| | Standard Deviation: 10.5 Seconds |
| | Relative Standard Deviation: 33.7% |

Rapid Dissolve Pouches—Nicotine

Tests were run using the lip balm of Example 7. The results are shown in Table 1-5. For Table 1, rapid dissolve mesh pouches were filled with the lip balm. The lip balm was given by sublabial administration of the pouch to five (5) test subjects who were trained to detect and note the time to sense the nicotine in their system (the time to satisfaction). The time for satisfaction data is shown in Table 1, below.

In Table 1, the lip balm was a lump placed in the pouch.

TABLE 1

| Time to Satisfaction (s) | | |
| --- | --- | --- |
| 4 mg Dose | 6 mg Dose | 9 mg Dose |
| 17 | 10 | 12 |
| 12 | 12 | 13 |
| 15 | 14 | 10 |
| 15 | 11 | 14 |
| 20 | 17 | 16 |

The taste, texture and acceptability were evaluated as well, and found to be acceptable.

Molded Pieces of Lip Balm

Mini chips of lip balm (100 mg lip balm chips containing 2 mg of nicotine per chip) were administered sublabial to five (5) test subjects who were trained to detect and note the time to sense the nicotine in their system (the time to satisfaction). The time for satisfaction data is shown in Table 2, below.

TABLE 2

| Time to Satisfaction (s) |
| --- |
| 2 mg Dose |
| 12 |
| 12 |
| 14 |
| 17 |
| 8 |

Flat discs of lip balm (200 mg lip balm chips containing 4 mg of nicotine per chip) were administered sublabial to five (5) test subjects who were trained to detect and note the time to sense the nicotine in their system (the time to satisfaction). The time for satisfaction data is shown in Table 3, below.

TABLE 3

| Time to Satisfaction (s) |
| --- |
| 10 |
| 7 |
| 12 |
| 8 |
| 11 |

Rounded drops of lip balm (400 mg lip balm chips containing 9 mg of nicotine per drop) were administered sublabial to five (5) test subjects who were trained to detect and note the time to sense the nicotine in their system (the time to satisfaction). The time for satisfaction data is shown in Table 4, below.

TABLE 4

| Time to Satisfaction (s) |
| --- |
| 20 |
| 17 |
| 22 |
| 25 |
| 18 |

Larger flat discs of lip balm (500 mg lip balm discs containing 10 mg of nicotine per drop) were administered sublabial to five (5) test subjects who were trained to detect and note the time to sense the nicotine in their system (the time to satisfaction). The time for satisfaction data is shown in Table 5, below.

TABLE 5

| Time to Satisfaction (s) |
| --- |
| 15 |
| 15 |
| 17 |
| 12 |
| 11 |

The taste and mouth feel for each of the above samples were found to be acceptable.

Rapid Dissolve Pouch—Caffeine

The lip balm of Example 4 was tested, and the data is shown in Tables 6-12. For Table 6, rapid dissolve mesh pouches were filled with the lip balm formula of Example 4, 500 mg lip balm containing 70 mg of caffeine. The lip balm was given by sublabial administration to five (5) test subjects who were trained to detect and note the time to sense the caffeine in their system (the time to satisfaction). The time to satisfaction data is shown below.

TABLE 6

| Time to Satisfaction (s) |
| --- |
| 25 |
| 25 |
| 31 |
| 22 |
| 30 |

For Table 7, rapid dissolve mesh pouches were filled with the lip balm formula of Example 4, 400 mg lip balm containing 56 mg of caffeine. The lip balm was given by sublabial administration to five (5) test subjects who were trained to detect and note the time to sense the caffeine in their system (the time to satisfaction). The time for satisfaction data is shown, below.

TABLE 7

| Time to Satisfaction (s) |
| --- |
| 21 |
| 22 |
| 30 |
| 24 |
| 26 |

For Table 8, rapid dissolve mesh pouches were filled with the lip balm formula of Example 4, 300 mg lip balm containing 42 mg of caffeine. The lip balm was given by sublabial administration to five (5) test subjects who were trained to detect and note the time to sense the caffeine in their system (the time to satisfaction). The time for satisfaction data is shown below.

TABLE 8

| Time to Satisfaction (s) |
| --- |
| 28 |
| 23 |
| 30 |
| 31 |
| 24 |

Molded Pieces of Lip Balm

Mini chips of lip balm (100 mg lip balm chips containing 14 mg of caffeine per chip) were administered sublabial to five (5) test subjects who were trained to detect and note the time to sense the caffeine in their system (the time to satisfaction). The time for satisfaction data is shown in Table 9, below.

TABLE 9

| Time to Satisfaction (s) |
| --- |
| 38 |
| 42 |
| 45 |
| 30 |
| 31 |

Chips of lip balm (200 mg lip balm chips containing 28 mg of caffeine per chip) were administered sublabial to five (5) test subjects who were trained to detect and note the time to sense the caffeine in their system (the time to satisfaction). The time for satisfaction data is shown in Table 10, below.

TABLE 10

| Time to Satisfaction (s) |
| --- |
| 25 |
| 29 |
| 35 |
| 30 |
| 27 |

Flat discs of lip balm (400 mg lip balm chips containing 56 mg of caffeine per chip) were administered sublabial to five (5) test subjects who were trained to detect and note the time to sense the caffeine in their system (the time to satisfaction). The time for satisfaction data is shown in Table 11, below.

TABLE 11

| Time to Satisfaction (s) |
| --- |
| 21 |
| 25 |
| 30 |
| 27 |
| 22 |

Flat discs of lip balm blended with hard cinnamon candy (400 mg lip balm chips containing 52 mg of caffeine per chip) were administered sublabial to five (5) test subjects who were trained to detect and note the time to sense the caffeine in their system (the time to satisfaction). The time for satisfaction data is shown in Table 12, below.

TABLE 12

| Time to Satisfaction (s) |
| --- |
| 18 |
| 20 |
| 23 |
| 19 |
| 28 |

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A lip balm formulation for applying to a lip consisting of:
    at least one lipid, a surfactant, and a caffeine active,
    wherein the lip balm formulation contains from about 25 to 60 wt. % of the surfactant based on the total weight of the formulation;
    wherein the surfactant consists of a mixture of mono- and diglycerides and propylene glycol;
    wherein the surfactant has an HLB of 4;
    wherein the lip balm formulation contains from about 60 to 30 wt. % of the at least one lipid based on the total weight of the formulation;

wherein the at least one lipid comprises hydrogenated palm oil; and wherein the surfactant minimizes the surface tension of the at least one lipid.

2. The lip balm of claim 1, wherein the w/w ratio of the surfactant to the at least one lipid is in the range of from about 3/1 to 1/3.

3. A lip balm formulation for applying to a lip consisting of:
- at least one lipid, a surfactant, and a caffeine active;
- wherein the at least one lipid is in the range of about 30 wt. % to 60 wt. % based on the total weight of the formulation;
- wherein the at least one lipid comprises hydrogenated palm oil;
- wherein the surfactant is in the range of about 60 wt. % to 25 wt. % based on the total weight of the formulation;
- wherein the caffeine is in the range of about 1 to 40 wt. % based on the total weight of the formulation;
- an excipient selected from the group consisting of a stabilizer, a melting point adjuster, an oil, a flavoring, a sun screen, a pharmaceutical and glycerin;
- wherein the surfactant consists of a mixture of mono- and diglycerides and propylene glycol with an HLB of 4; and
- wherein the surfactant minimizes the surface tension of the at least one lipid.

4. The lip balm formulation of claim 3, wherein the stabilizer comprises glyceryl tristearate.

5. The lip balm formulation of claim 1, and
wherein the lip balm formulation, when applied to the lip, delivers the caffeine active in less than about one minute.

6. The lip balm of claim 1, wherein the caffeine active is present in the range of about 1 to 40 wt. % based on the total weight of the formulation.

7. The lip balm formulation of claim 3, wherein the w/w ratio of the surfactant to the at least one lipid is in the range of from about 3/1 to 1/3.

8. The lip balm formulation of claim 1, wherein the caffeine active is a solid caffeine of micronized particles.

9. The lip balm formulation of claim 3, wherein the caffeine active is a solid caffeine of micronized particles.

10. The lip balm formulation of claim 1, wherein the lip balm formulation, when applied to the lip, delivers the caffeine active in less than about ten minutes.

11. The lip balm formulation of claim 3, wherein the lip balm formulation, when applied to the lip, delivers the caffeine active in less than about one minute.

12. The lip balm formulation of claim 3, wherein the lip balm formulation, when applied to the lip, delivers the caffeine active in less than about ten minutes.

* * * * *